United States Patent [19]

Laird

[11] Patent Number: 4,683,882
[45] Date of Patent: Aug. 4, 1987

[54] ENDROTRACHEAL TUBE HOLDER

[76] Inventor: Jesse S. Laird, 15461 Camarillo St., Sherman Oaks, Calif. 91403

[21] Appl. No.: 796,260

[22] Filed: Nov. 8, 1985

[51] Int. Cl.$^4$ ............................................. A61M 25/02
[52] U.S. Cl. ...................... 128/207.17; 128/DIG. 26; 604/179
[58] Field of Search ...................... 128/200.26, 207.14, 128/207.17, DIG. 26; 604/174, 179

[56] References Cited

U.S. PATENT DOCUMENTS

| | | | |
|---|---|---|---|
| 2,693,182 | 11/1954 | Phillips | 128/200.26 |
| 3,834,380 | 9/1974 | Boyd | 604/180 |
| 4,114,626 | 9/1978 | Beran | 128/DIG. 26 |
| 4,449,527 | 5/1984 | Hinton | 128/207.17 |
| 4,516,293 | 5/1985 | Beran | 128/207.17 |
| 4,516,958 | 5/1985 | Marshall et al. | 604/174 |

Primary Examiner—Henry J. Recla
Attorney, Agent, or Firm—Rober A. Marrs

[57] ABSTRACT

A medical tube holder is disclosed herein having a base supporting an adhesive strap for adherence to the facial area of a patient immediately adjacent the mouth. The base is provided with a central opening for receiving and holding an elongated tube or straw-like member inserted into the patient's mouth. An adjustable clamp releasably secures the tube or straw-like member in place on the holder. Various clamp constructions are employed such as a gate type, a C-clamp or a notched strap type.

1 Claim, 6 Drawing Figures

ENDOTRACHEAL TUBE HOLDER

BACKGROUND OF THE INVENTION

1. Field of the Invention

The present invention relates to medical tube holders and, more particularly, to a novel endotracheal tube holder employed to secure an endotracheal tube to a patient's facial area.

2. Brief Description of the Prior Art

In the medical field, endotracheal tubes are frequently placed into the mouth of the patient or a variety of medical procedures. It is important that such a tube or straw-like member be retained in position so that the patient cannot remove the tube or inadvertently dislodge the tube from its in-place position. This is especially important when the patient is an infant or toddler.

Furthermore, in the event the patient is unconscious, the tube placement cannot be disturbed through any inadvertent movement of the patient undergoing the procedure. Although some holders have been employed for retaining medical devices onto limbs of a patient, such holders are relatively cumbersome to use, uncomfortable for the patient and are generally not classed as disposable items. Comfort and ease of handling are particularly important when dealing with infants or small children.

Therefore, a longstanding need has existed to provide a holder for releasably securing an endotracheal tube in proper position which has been inserted into the mouth of a patient.

SUMMARY OF THE INVENTION

Accordingly, the above problems and difficulties are obviated by the present invention which provides a novel endotracheal tube holder for retaining such a tube in proper position with respect to the mouth of the patient and which includes a base means having an adhesive strap portion outwardly extending from opposite sides of the base means intended to releasably support the holder on the facial area of the user. The base means further includes a central opening for receiving the tube and a clamping means carried on the base means releasably holds the tube to the base means in position with respect to the mouth of the patient. In one form of the invention, the clamp means includes a gate type clamp which converts rotary movement into linear movement of a clamp member merging the tube against the base means. Another form includes a C-clamp having a thumb screw arrangement for tightening the clamp about the tube to retain it in position while another version includes a strap carried on the base means having a notched end passing through an aperture in a single direction so as to tighten about the tube for retention in position.

Therefore, it is among the primary objects of the present invention to provide a novel endotracheal tube holder that may releasably hold such a tube in position with respect to the mouth of the patient and that is convenient to use as well as economical to manufacture.

Another object of the present invention is to provide a novel tube holder for supporting an endotracheal tube which has been inserted into a patient's mouth so that an inadvertent movement of the patient will not dislodge or remove the tube from its position.

Another object of the present invention is to provide a novel tube holder for supporting an endotracheal tube that may be readily installed about the facial area of a patient using adhesive retaining means and which further includes a releasable clamp for securing the tube in position with respect to the facial area.

Still a further object of the present invention is to provide a novel holder for an endotracheal tube that may employ a variety of clamping means for retaining the tube in position and which further includes releasable means for removing the device from the facial area of the patient particularly after the completion of the medical procedure.

Yet another object of the present invention is to provide a novel holder for an endotracheal tube that may be readily used by infants or small children whereby the tube is releasably held in position during the performance of the medical procedure and where inadvertent movements will not dislodge or remove the tube from its preferred position.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood by reference to the following description, taken in connection with the accompanying drawings in which:

DESCRIPTION OF THE PREFERRED EMBODIMENTS

Figure 1:
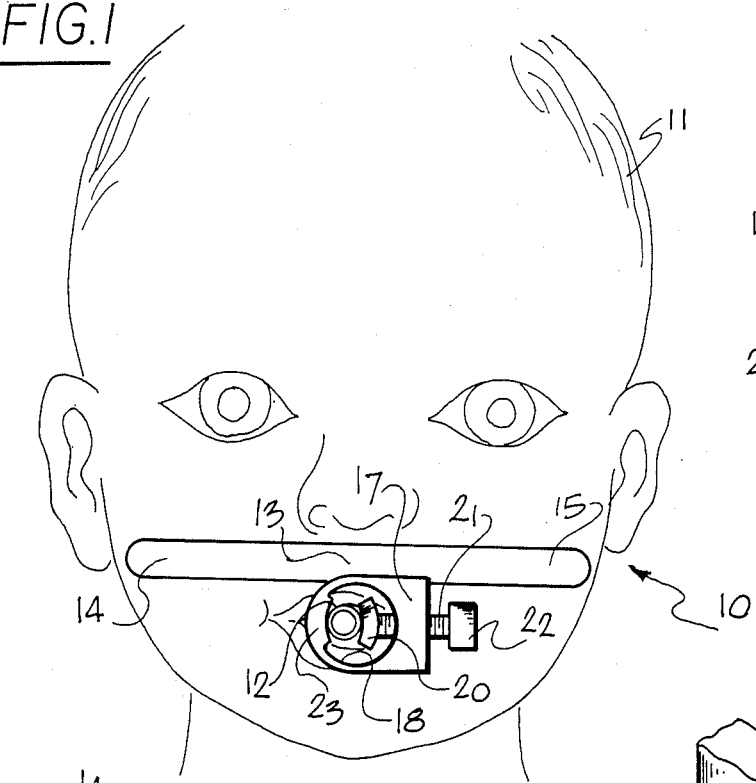
FIG. 1 is a front elevational view of an infant patient using the novel endotracheal tube holder of the present invention.

Referring to FIG. 1, the novel endotracheal tube holder of the present invention is illustrated in the general direction of arrow 10 which is illustrated as being applied to the facial area of an infant 11 immediately adjacent to the mouth so as to support an endotracheal tube 12 during a medical procedure. The tube 12 is initially inserted into the mouth of the patient preparatory to the procedure and the tube is releasably held in position by the holder 10.

The holder 10 includes a base for support means 13 which has a strap on its back side outwardly extending from the opposite sides in the form of strap portions 14 and 15. The back side of the strap is provided with a low contact adhesive, indicated by numeral 16 in FIG. 3, for removably securing the holder to the facial area of the patient 11. The strap means is flexible so as to conform to the contour of the facial area and the support or base means 13 is attached to the straps in an integral fashion during fabrication so that a unitary construction is produced.

Downwardly depending from the base or support means is a portion 17 having a central opening 18 substantially coaxially disposed with respect to the mouth of the patient 11. The straw 12 passes through the opening 18 and a clamp means releasably retains the tube 12 in position against the support portion 17. In one form, the clamp means includes a plate 20 carried on the end of a lead screw 21 which is threadably disposed through the wall of the support portion 17. A turning knob 22 is carried on the free end of the lead screw 21 so that when the knob is rotated by the fingers of an attendant, the lead screw will move in a linear manner to merge the plate 20 into contact with the tube 12. The opposite side of the tube will be merged against a back-up portion 23 of the support means. In order to remove the holder, the thumb screw 22 is reversed so that the clamp plate 20 is withdrawn and the tube 12 freed from the holder. The tube can now be removed from the patient and the holder can be removed from the facial area.

Figure 2:
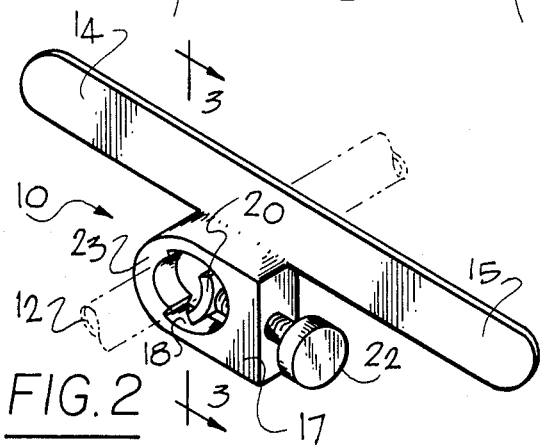
FIG. 2 is a front perspective view of the endotracheal tube holder shown in FIG. 1.

Referring now in detail to FIG. 2, it can be seen that the holder 10 has a clamping means wherein the clamp plate 20 presents a curved surface intended to bear against the curved surface of the tube 12 while the surface of portion 23 is similarly curved to conform and accommodate the curved surface on the opposite side of the tube 12. Furthermore, the portion 23 is thickened so as to provide for a firm and positive bearing surface or engaging surface against which the tube can be pressed by the clamp means. FIG. 2 also illustrates that the strap means represented by portions 14 and 15 are integrally formed with the base or support means 17 and that the base or support means 17 includes the central opening 18.

Figure 3:
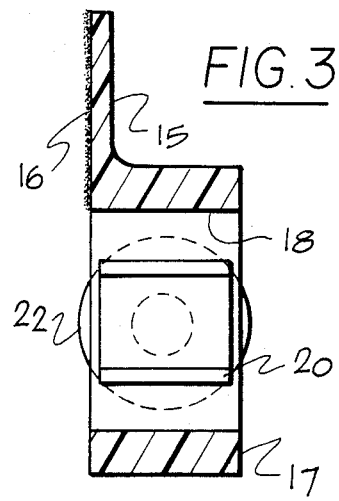
FIG. 3 is a transverse cross-sectional view of the endotracheal tube holder shown in FIG. 2 as taken in the direction of arrows 3—3 thereof.

Referring now in detail to FIG. 3, it can be seen that the back side of the strap means 15, as well as 14, includes an adhesive layer 16. Also, it can be seen that the strap means as well as the base of the support means 17 is integrally formed from material such as plastic or the like. Therefore, an integral molded part may be employed which is composed of inexpensive material so that the entire unit may be described as disposable after initial use.

Figure 4:
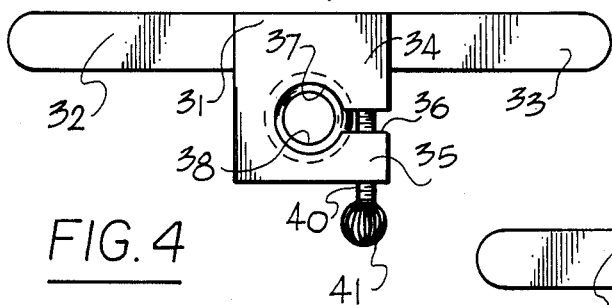
FIG. 4 is a front elevational view of another embodiment of the present invention incorporating a C-clamp.

Referring now in detail to FIG. 4, another embodiment of the present invention is illustrated in the general direction of arrow 30 which comprises a body portion 31 and a pair of strap portions 32 and 33 similar to those previously described. However, the clamp means is different inasmuch as the clamp means takes the form of a C-clamp taking the form of legs 34 and 35 which are joined together with the portion 31. The legs are separated by a space 36 leading into a central opening 37 which is partially occupied by a resilient grommet 38. The grommet 38 includes a central opening through which the endotracheal tube is located. Different sized tubes may be accommodated by different sized grommets and retention of the grommet to the tube is established by means of a rotatable lead screw 40 having a finger knob 41. The lead screw is disposed between the legs 34 and 35 so that when rotated, the legs come together about the grommet 38 which, in turn, bears about the periphery of the tube 12. In order to properly locate the grommet with respect to the opening 37, a circular surface is provided in the base or support means 31 defining the opening which mounts the grommet 38.

Figure 6:
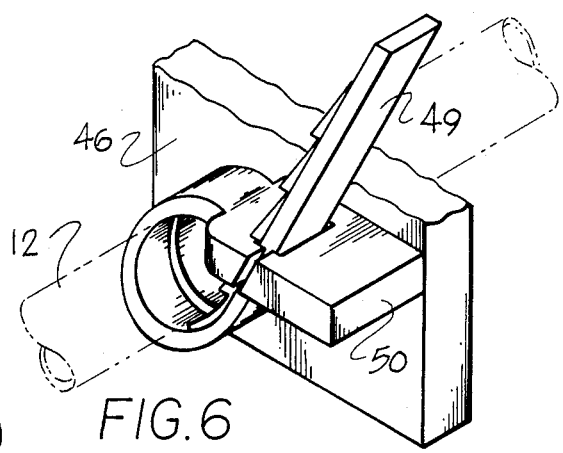
FIG. 6 is a front perspective view of the embodiment shown in FIG. 5.
Figure 5:
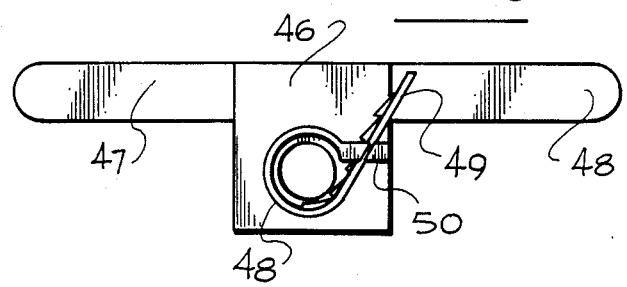
FIG. 5 is a front elevational view of another embodiment of the present invention incorporating a notched strap clamp for holding an endotracheal tube.

Referring now in detail to FIGS. 5 and 6, still another embodiment of the invention is illustrated in the general direction of arrow 45 which takes the form of a space or support means 46 having strap portions 47 and 48 adhesively adapted to engage and secure with the facial area of the patient as previously described. The support or base means 46 includes a central opening through which the tube 12 is disposed and a strap means is used as a clamp means for retaining the tube in position. The strap means includes a flexible strap 48 having a notched end 49 which passes through an opening in a keeper 50. The notch end 49 is pulled through the keeper 50 until the strap is taut about the straw or tube 12. Loosening of the strap is prevented because of the notches engaging against the keeper 50. However, release may be intentionally obtained by pulling the strap 49 in a lateral direction so as to separate the notch from the keeper and permitting the strap to slide through the keeper to loosen about the tube.

In view of the foregoing, it can be seen that the holder of the present invention may be readily attached to the facial area of a patient and that a tube 12 may be readily retained and supported thereby. A variety of clamping means may be employed for releasably holding the tube in position and the entire holder may be disposed of once used after an operating or medical procedure.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. An endotracheal tube holder adapted to be applied to the facial area of a patient to retain and support such a tube comprising the combination of:

a base means having a central opening therein accommodating passage of said tube;

attachment means mounted on said base means for removable securement to the facial area of the patient;

adjustable clamp means operably carried on said base means for releasably coupling to said tube to positively retain said tube in position with respect to the patient's facial area;

said attachment means includes elongated straps or strips outwardly extending from opposite sides of said base means and extending no more than the facial area of the patient;

an adhesive layer of low contact adhesive carried on the backside of said straps or strips;

said clamp means includes manual adjustment means carried on said base means for tightening and loosening said clamp means about said tube allowing said clamp means to advance or retract about said tube;

said clamp means includes a C-shaped clamp having a pair of legs separated by a gap leading into said central opening; and a screw means interconnecting said legs to close said C-shaped clamp about said tube;

said clamp means further includes a resilient grommet of constant inner diameter in said central opening to partially reduce its diameter so as to frictionally engage with and support said tube in response to actuation of said adjustable clamp means.

* * * * *